(12) United States Patent
Luzung et al.

(10) Patent No.: US 9,890,128 B2
(45) Date of Patent: Feb. 13, 2018

(54) PROCESS FOR MAKING SUBSTITUTED QUINAZOLINE COMPOUNDS

(71) Applicants: Michael Luzung, Jersey City, NJ (US); Guy Humphrey, Hillsborough, NJ (US); Bangping Xiang, Bridgewater, NJ (US); Kevin M. Belyk, Metuchen, NJ (US); Stephen Mark Dalby, Hertfordshire (GB); Wilfried Schwab, Wuppertal (DE); Burkhard Klenke, Wuppertal (DE); Tom Moody, Armagh (GB); Gareth Brown, Armagh (GB)

(72) Inventors: Michael Luzung, Jersey City, NJ (US); Guy Humphrey, Hillsborough, NJ (US); Bangping Xiang, Bridgewater, NJ (US); Kevin M. Belyk, Metuchen, NJ (US); Stephen Mark Dalby, Hertfordshire (GB); Wilfried Schwab, Wuppertal (DE); Burkhard Klenke, Wuppertal (DE); Tom Moody, Armagh (GB); Gareth Brown, Armagh (GB)

(73) Assignees: MERCK SHARP & DOHME CORP., Rahway, NJ (US); AICURIS ANTI-INFECTIVE CURES GMBH, Wuppertal (DE)

( * ) Notice: Subject to any disclaimer, the term of this patent is extended or adjusted under 35 U.S.C. 154(b) by 0 days.

(21) Appl. No.: 15/102,417

(22) PCT Filed: Dec. 8, 2014

(86) PCT No.: PCT/US2014/068981
§ 371 (c)(1),
(2) Date: Jun. 7, 2016

(87) PCT Pub. No.: WO2015/088931
PCT Pub. Date: Jun. 18, 2015

(65) Prior Publication Data
US 2016/0311781 A1    Oct. 27, 2016

Related U.S. Application Data

(60) Provisional application No. 61/915,142, filed on Dec. 12, 2013.

(51) Int. Cl.
C07D 239/84 (2006.01)
B01J 31/02 (2006.01)
C07D 295/125 (2006.01)

(52) U.S. Cl.
CPC ........ *C07D 239/84* (2013.01); *B01J 31/0202* (2013.01); *B01J 31/0232* (2013.01); *B01J 31/0244* (2013.01); *B01J 31/0271* (2013.01); *C07D 295/125* (2013.01); *B01J 2231/324* (2013.01)

(58) Field of Classification Search
CPC .............................. C07D 239/84; B01J 31/02
See application file for complete search history.

(56) References Cited

U.S. PATENT DOCUMENTS

| 7,196,086 B2 | 3/2007 | Wunberg et al. |
| 7,960,387 B2 | 6/2011 | Wunberg et al. |
| 8,084,604 B2 | 12/2011 | Gooβen et al. |
| 8,513,255 B2 | 8/2013 | Wunberg et al. |
| 2015/0045371 A1 | 2/2015 | Maertens et al. |

*Primary Examiner* — Kahsay Habte
(74) *Attorney, Agent, or Firm* — Jeffrey P. Bergman; Catherine D. Fitch

(57) ABSTRACT

The present invention is directed to a process for making Substituted Quinazoline Compounds of formula (I): which are useful for the treatment and prophylaxis of HCMV infection. The present invention is also directed to compounds that are useful as synthetic intermediates for making the compounds of formula (I).

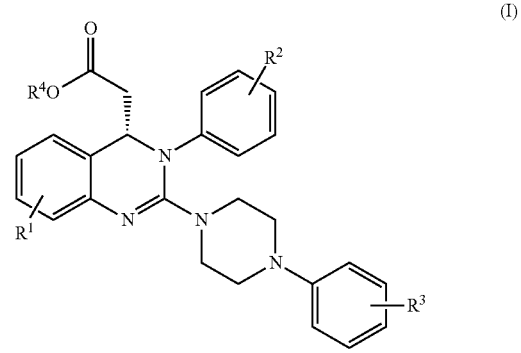

(I)

16 Claims, No Drawings

PROCESS FOR MAKING SUBSTITUTED QUINAZOLINE COMPOUNDS

CROSS-REFERENCE TO RELATED APPLICATIONS

This application is the national stage application under 35 U.S.C. 371 of International Patent Application No. PCT/US14/068981, filed Dec. 8, 2014, which claims priority to U.S. Provisional Patent Application No. 61/915,142, filed Dec. 12, 2013. Each of the aforementioned PCT and provisional applications is incorporated by reference in its entirety.

FIELD OF THE INVENTION

The present invention is directed to a process for making Substituted Quinazoline Compounds which are useful for the treatment or prophylaxis of HCMV infection. The present invention is also directed to compounds that are useful as synthetic intermediates in the process of the invention.

BACKGROUND OF THE INVENTION

Human cytomegalovirus (HCMV) is ubiquitously distributed in the human population. In immunocompetent adults infections are mainly asymptomatic, but in immunocompromised patients, such as transplant recipients or AIDS patients, life threatening infections occur at a high rate. HCMV is also the leading cause of birth defects among congenitally transmitted viral infections.

Various substituted heterocyclic compounds are inhibitors of the HCMV terminase enzyme. Included in these heterocycles are quinazolines related to Compound A, as defined and described below. These compounds and pharmaceutically acceptable salts thereof are useful in the treatment or prophylaxis of infection by HCMV and in the treatment, prophylaxis, or delay in the onset or progression of HCMV infection. Representative quinazoline compounds that are useful for treating HCMV infection are described, for example, in U.S. Pat. No. 7,196,086. Among the compounds disclosed in U.S. Pat. No. 7,196,086, is (S)-2-(8-fluoro-3-(2-methoxy-5-(trifluoromethyl)phenyl)-2-(4-(3-methoxyphenyl)piperazin-1-yl)-3,4-dihydroquinazolin-4-yl)acetic acid, hereinafter referred to as Compound A. Compound A is a known inhibitor of HCMV terminase. The structure of Compound A is as follows:

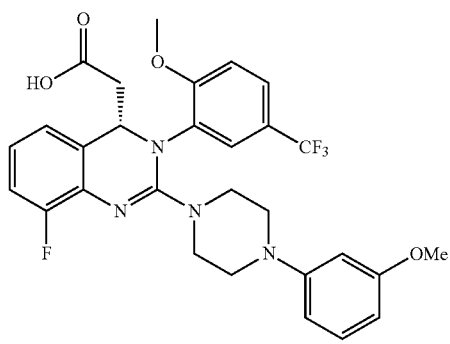

Compound A

U.S. Pat. Nos. 7,196,086 and 8,084,604 disclose methodology that can be employed to prepare Compound A and related quinazoline-based HCMV terminase inhibitors. These methods are practical routes for the preparation of Compound A and related heterocyclic compounds.

SUMMARY OF THE INVENTION

The present invention is directed to a process for making Substituted Quinazoline Compounds of Formula (I) which are useful for the treatment and prophylaxis of HCMV infection. More particularly, the present invention includes a process (alternatively referred to herein as "Process A") for preparing a compound of Formula I:

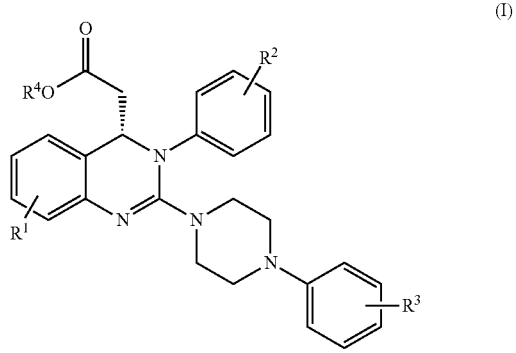

(I)

wherein said process comprises contacting a compound of formula (viii):

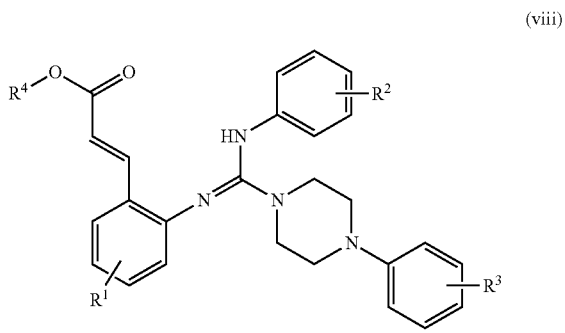

(viii)

or a salt thereof, with a phase-transfer catalyst and a base, in a mixture of water and organic solvent A, for a time sufficient to form a compound of formula (I), wherein:

$R^1$ represents up to 3 phenyl group substituents, each independently selected from $C_1$-$C_6$ alkyl, $C_1$-$C_6$ haloalkyl, halo, —CN, —OH and $C_1$-$C_6$ alkoxy;

$R^2$ represents up to 3 phenyl group substituents, each independently selected from $C_1$-$C_6$ alkyl, $C_1$-$C_6$ haloalkyl, halo, —CN, —OH and $C_1$-$C_6$ alkoxy;

$R^3$ represents up to 3 phenyl group substituents, each independently selected from $C_1$-$C_6$ alkyl, $C_1$-$C_6$ haloalkyl, halo, —CN, —OH and $C_1$-$C_6$ alkoxy; and $R^4$ is $C_1$-$C_6$ alkyl or $C_3$-$C_7$ cycloalkyl, and wherein organic solvent A is selected from toluene, DCM, MTBE, 2-methyltetrahydrofuran, xylenes, ethyl acetate, isopropyl acetate, acetonitrile and mixtures thereof.

Other embodiments, aspects and features of the present invention are either further described in or will be apparent from the ensuing description, examples, and appended claims.

DETAILED DESCRIPTION OF THE INVENTION

The present invention is directed to a process for making Substituted Quinazoline Compounds of Formula (I) which are useful for inhibiting the replication of HCMV and for the treatment or prophylaxis of HCMV infection.

Definitions and Abbreviations

The term "alkyl" as used herein, refers to an aliphatic hydrocarbon group, having from 1 to 20 carbon atoms wherein one of its hydrogen atoms is replaced with a bond. An alkyl group may be straight or branched. In one embodiment, an alkyl group has from 1-6 carbon atoms ("$C_1$-$C_6$alkyl"). In another embodiment, an alkyl group has from 1-4 carbon atoms ("$C_1$-$C_4$alkyl"). Non-limiting examples of $C_1$-$C_6$ alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. Non-limiting examples of $C_1$-$C_4$ alkyl groups include methyl, ethyl, n-propyl, isopropyl, n-butyl, sec-butyl, isobutyl and tert-butyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, a $C_1$-$C_6$ alkyl group is linear. In another embodiment, a $C_1$-$C_6$ alkyl group is branched. Unless otherwise indicated, a $C_1$-$C_6$ alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms ("C2-C6 alkenyl"). Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "$C_1$-$C_6$ hydroxyalkyl" as used herein, refers to $C_1$-$C_6$ alkyl group, as defined above, wherein one of the $C_1$-$C_6$ alkyl group's hydrogen atoms is replaced with a —OH group. A $C_1$-$C_6$ hydroxyalkyl group may be straight or branched and contain. Non-limiting examples of $C_1$-$C_6$ hydroxyalkyl groups include methanol, ethanol, isopropanol, and tert-butanol.

The term "$C_6$-$C_{10}$ aryl" refers to phenyl and naphthyl. In one embodiment, an aryl group is phenyl.

The term "3 to 7-membered cycloalkyl" refers to a refers to a non-aromatic mono- or ring system comprising from about 3 to about 7 ring carbon atoms. Examples of "3 to 7-membered cycloalkyls include cyclopropyl, cyclobutyl, cyclopentyl, cyclohexyl and cycloheptyl. A 3 to 7-membered cycloalkyl group can be optionally substituted with one or more "ring system substituents" which may be the same or different, and are as defined herein below. In one embodiment, a 3 to 7-membered cycloalkyl group is unsubstituted. A ring carbon atom of a 3 to 7-membered cycloalkyl may be functionalized as a carbonyl group. An illustrative example of such a 3 to 7-membered cycloalkyl (also referred to herein as a "cycloalkanoyl" group) includes, but is not limited to, cyclobutanoyl:

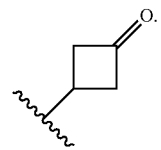

The term "halo" or "halogen" as used herein, refers to fluorine, chlorine, bromine and iodine (alternatively referred to as fluoro, chloro, bromo, and iodo).

The term "5 or 6-membered monocyclic heteroaryl," as used herein, refers to an aromatic monocyclic ring system comprising about 5 to about 6 ring atoms, wherein from 1 to 4 of the ring atoms is independently O, N or S and the remaining ring atoms are carbon atoms. A 5 or 6-membered monocyclic heteroaryl group can be optionally substituted by one or more "ring system substituents" which may be the same or different, and are as defined herein below. A 5 or 6-membered monocyclic heteroaryl group is joined via a ring carbon atom, and any nitrogen atom of a heteroaryl can be optionally oxidized to the corresponding N-oxide. The term "5 or 6-membered monocyclic heteroaryl" also encompasses a 5 or 6-membered monocyclic heteroaryl group, as defined above, which is fused to a benzene ring. Non-limiting examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzimidazolyl, benzothienyl, imidazolyl, benzimidazolyl, thienopyridyl, thienopyrimidyl, pyrrolopyridyl, imidazopyridyl, isoquinolinyl, 1,2,4-triazinyl, benzothiazolyl and the like, and all isomeric forms thereof. Unless otherwise indicated, a 5 or 6-membered monocyclic heteroaryl group is unsubstituted.

The term "9 or 10-membered bicyclic heteroaryl," as used herein, refers to an aromatic bicyclic ring system comprising about 9 to about 10 ring atoms, wherein from 1 to 4 of the ring atoms is independently O, N or S and the remaining ring atoms are carbon atoms. A 9 or 10-membered bicyclic heteroaryl group can be optionally substituted by one or more "ring system substituents" which may be the same or different, and are as defined herein below. A 9 or 10-membered bicyclic heteroaryl group is joined via a ring carbon atom, and any nitrogen atom of a heteroaryl can be optionally oxidized to the corresponding N-oxide. Non-limiting examples of 9 or 10-membered bicyclic heteroaryls include and the like, and all isomeric forms thereof. Unless otherwise indicated, a 9 or 10-membered bicyclic heteroaryl group is unsubstituted.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited above are inclusive; i.e., the range includes the values for the upper and lower limits of the range as well as all values in between.

When any variable occurs more than one time in a compound involved in the process of the invention (e.g., $R^f$), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds employed as reactants or reagents in the process of the invention (e.g., Compounds II, III, and IV), a "stable" compound is one whose structure and properties remain or can be caused to remain essentially unchanged for a period of time sufficient to allow its use in the process of the invention so as to achieve the preparation of Compound of Formula (I). In reference to Compound of Formula (I), a "stable" compound is a compound which can be prepared in accordance with the process of the present invention and then isolated and whose structure and properties remain or can be caused to remain essentially unchanged for a period of time sufficient to allow use of the compound for its intended purpose; e.g., for the therapeutic administration to a subject who has HCMV infection.

The following abbreviations are used below and have the following meanings: t-Bu is tertiary butyl, DCM is dichloromethane, DTTA is Di-P-Toluoyl-D-tartaric acid, HPLC is high performance liquid chromatography, IPAC is isopropyl acetate; LC/MS is liquid chromatography/Mass pMTBE is methyl tert-butyl ether; pin is pinacol, THF is tetrahydrofuran and TLC is thin-layer chromatography.

The Processes of the Present Invention

The present invention is directed to a process for making Substituted Quinazoline Compounds of Formula (I) which are useful for inhibiting the replication of HCMV and for the treatment or prophylaxis of HCMV infection. One aspect of the present invention is the process for making Compounds of Formula (I) as set forth above in the Summary of the Invention ("Process A").

In another aspect, the present invention provides synthetic intermediates useful in the processes of the present invention.

In one embodiment process A further comprises the step of making the compound of formula (viii) ("Process B")

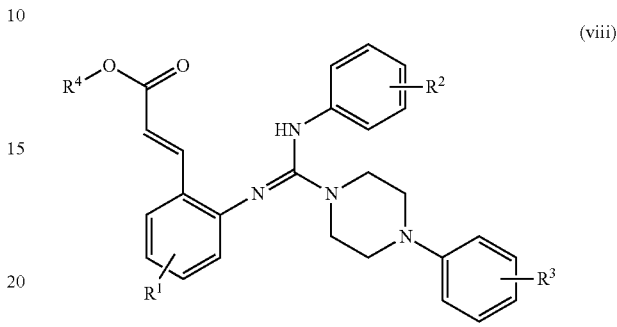

(viii)

wherein said process comprises the steps:
(A) contacting a compound of Formula (v):

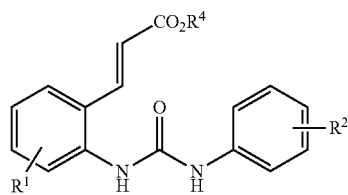

with a dehydrating agent and a base in an organic solvent B, for a time sufficient to provide an intermediate compound of Formula (vi):

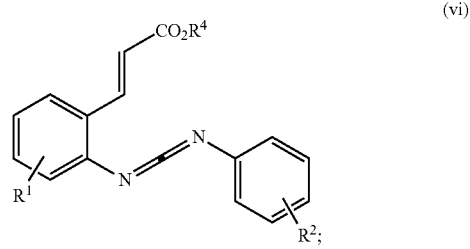

(vi)

and
(B) contacting the intermediate compound of formula (vi) with a compound of formula (vii):

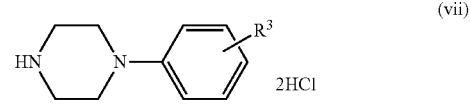

(vii)

in the presence of a base, in a mixture of water and organic solvent B', for a time sufficient to provide a compound of formula (viii), wherein organic solvents B and B' are each independently selected from ethyl acetate, isopropyl acetate, THF, 2-methyltetrahydrofuran, DCM, benzene, toluene, xylene, chlorobenzene, acetonitrile and dioxane.

In another embodiment, Process B further comprises the step (referred to herein as "Process C") of contacting the formed compound of formula (viii) with an acid, in a mixture of water and an organic solvent C for a time sufficient to form the corresponding acid salt of the compound of formula (viii), wherein organic solvent C is selected from toluene, DCM, MTBE, 2-methyltetrahydrofuran, xylenes, ethyl acetate, isopropyl acetate, acetonitrile and mixtures thereof, to provide the corresponding acid salt of the compound of formula (viii).

In one embodiment, for Process A, said process is conducted at a temperature in a range of from about −10° C. to about 30° C.;

the base used is selected from an alkali metal carbonate, an alkali metal hydrogen carbonate, an alkali metal bicarbonate, an alkali metal phosphate, an alkali metal hydrogen phosphate, an alkali metal hydroxide, a trialkylamine and an aromatic amine;

organic solvent A is selected from toluene, DCM, MTBE, 2-methyltetrahydrofuran, xylenes and mixtures thereof; and the phase transfer catalyst used is a compound of formula (PT1) or (PT2):

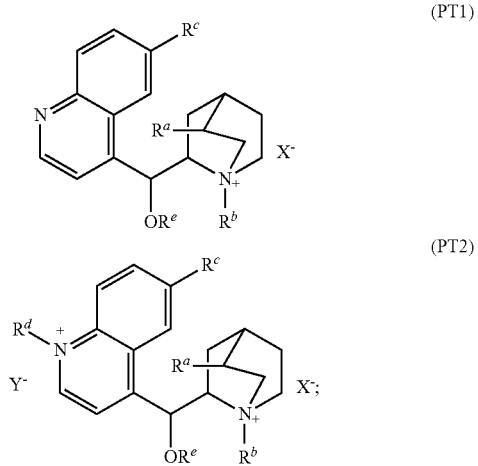

wherein:

$R^a$ is selected from ethyl and vinyl, $R^b$ is selected from $C_{1-6}$alkyl, $C_{2-6}$alkenyl, $C_{2-6}$alkynyl, $C_{3-6}$cycloalkyl, aryl, 5 or 6-membered monocyclic heteroaryl, 9 or 10-membered bicyclic heteroaryl, —$C_{1-4}$alkyl-aryl, —$C_{1-4}$alkyl-(5 or 6-membered monocyclic heteroaryl) and $C_{1-4}$alkyl-(9 or 10-membered bicyclic heteroaryl), wherein $C_{1-6}$alkyl, $C_{2-6}$alkenyl, $C_{2-6}$alkynyl, $C_{3-6}$cycloalkyl, aryl, heteroaryl and the aryl and heteroaryl portions of —$C_{1-4}$alkyl-aryl, —$C_{1-4}$alkyl-(5 or 6-membered monocyclic heteroaryl), and $C_{1-4}$alkyl-(9 or 10-membered bicyclic heteroaryl), are optionally substituted with one to five substituents independently selected from $R^f$, $R^c$ is selected from hydrogen, methoxy, halo, —CN, —$NO_2$ and —$CF_3$;

$R^d$ is selected from the group consisting of hydrogen, C(O)R, C(O)OR, CONRR', and $C_{1-6}$alkyl, $R^e$ is selected from $C_{1-6}$alkyl, $C_{2-6}$alkenyl, $C_{2-6}$alkynyl, $C_{3-6}$cycloalkyl, aryl, 5 or 6-membered monocyclic heteroaryl, 9 or 10-membered bicyclic heteroaryl, —$C_{1-4}$alkyl-aryl, —$C_{1-4}$alkyl-(5 or 6-membered monocyclic heteroaryl) and $C_{1-4}$alkyl-(9 or 10-membered bicyclic heteroaryl), wherein $C_{1-6}$alkyl, $C_{2-6}$alkenyl, $C_{2-6}$alkynyl, $C_{3-6}$cycloalkyl, aryl, heteroaryl and the aryl and heteroaryl portions of —$C_{1-4}$alkyl-aryl, —$C_{1-4}$alkyl-(5 or 6-membered monocyclic heteroaryl), and $C_{1-4}$alkyl-(9 or 10-membered bicyclic heteroaryl), are optionally substituted with one to five substituents independently selected from $R^f$, each occurrence of $R^f$ is independently selected from the group consisting of $C_{1-4}$alkyl, $C_{1-4}$haloalkyl, aryl, $C_{1-4}$alkoxy, hydroxy, CN, $CO_2R$, CONRR', SR, $SO_2R$, $SO_3R$, $PR_2$, $PO(OR)_2$, PO(OR) (NRR'), $PO(NRR')_2$, $P(OR)_2$, P(OR)(NRR'), $P(NRR')_2$, SiRR'R", $B(OR)_2$, C(O)R, NRR', $NO_2$, and halogen, each R, R' and R" is independently selected from the group consisting of, H, $C_{1-6}$alkyl, hydroxyl, $C_{1-6}$alkoxy, aryl, 5 or 6-membered monocyclic heteroaryl, 9 or 10-membered bicyclic heteroaryl, —$CH_2$-aryl, —$CH_2$-heteroaryl, and each X and Y are independently anions selected from halide, OH, $HSO_4$, $SO_4$, $BF_4$, $SbF_6$, carboxylate, carbonate, hydrogen carbonate, $NO_3$, sulfonate, hexafluorophosphate, phosphate, hydrogen phosphate and perchlorate.

In another embodiment for Process A, said process is conducted at a temperature in a range of from about −5° C. to about 10° C.;

the base used is selected from $K_2CO_3$, $KHCO_3$, $Na_2CO_3$, $NaHCO_3$, $Na_3PO_4$, $Na_2HPO_4$, $NaH_2PO_4$, $K_3PO_4$, $K_2HPO_4$ and $KH_2PO_4$;

the phase transfer catalyst used is selected from:

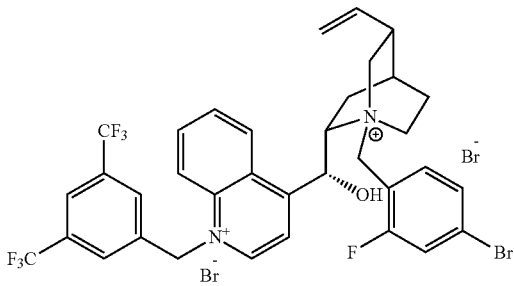

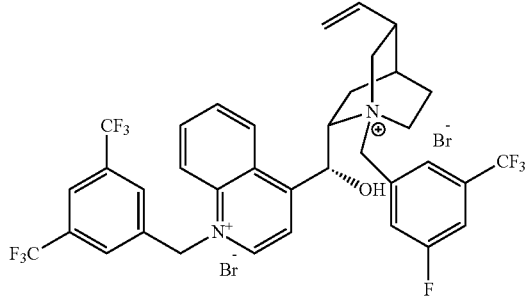

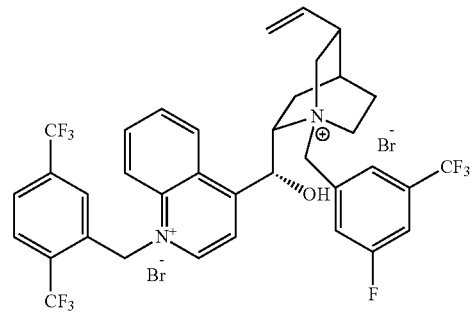

-continued
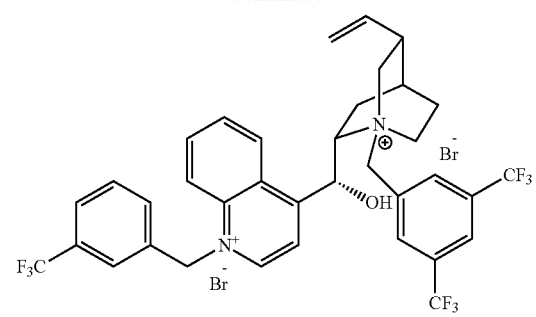
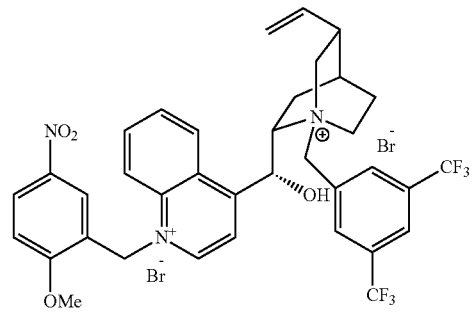
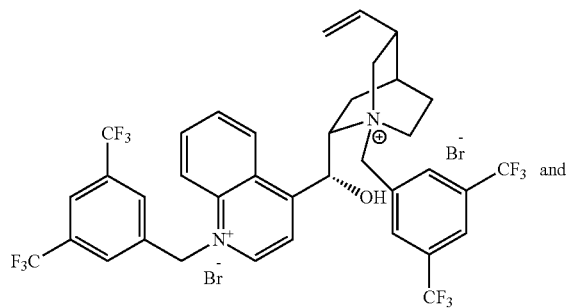
and
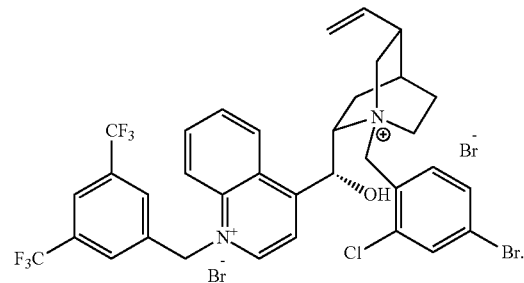
In another embodiment for Process A, the phase transfer catalyst used is selected from:
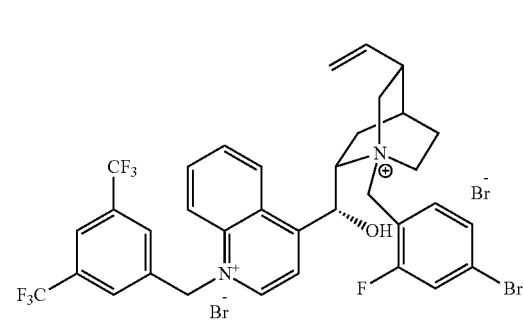
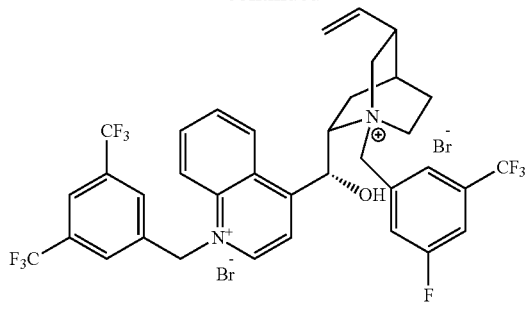
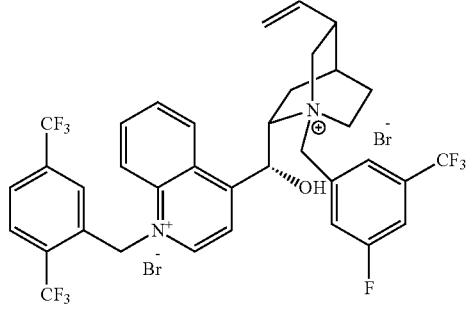
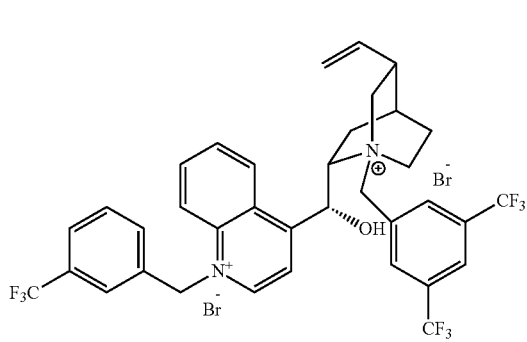
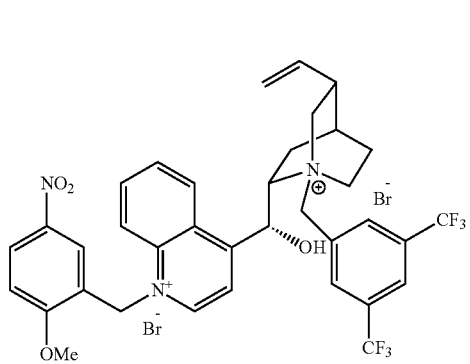
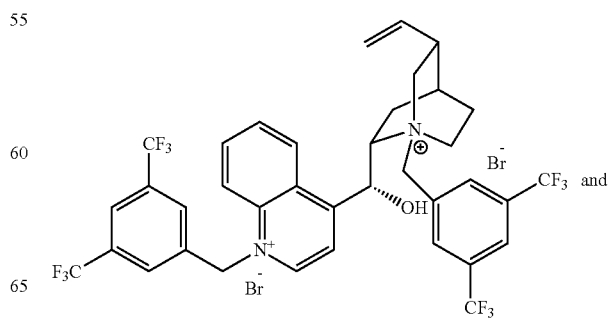
and -continued

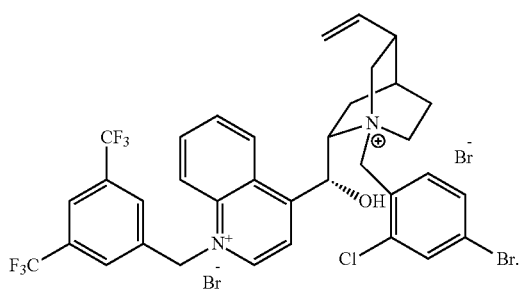

In another embodiment for Process A, the phase transfer catalyst used is

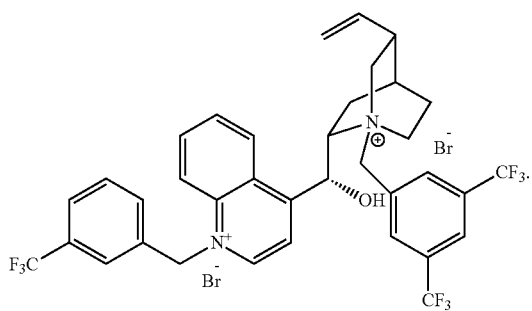 [SMILES: C=CC1C[N+]2(Cc3cc(C(F)(F)F)cc(C(F)(F)F)c3)CCC1CC2[C@H](O)c1cc[n+](Cc2cccc(C(F)(F)F)c2)c2ccccc12 ; [Br-] ; [Br-]]

In one embodiment for Process A, the compound of formula (I), or salt thereof, made by said process is:

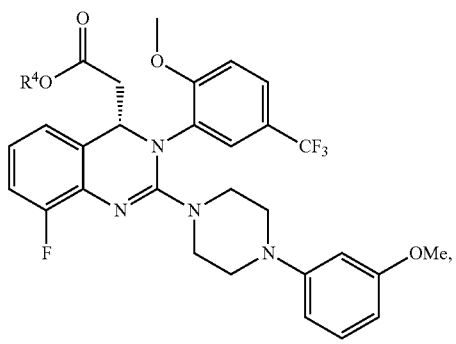

wherein $R^4$ is $C_1$-$C_6$ alkyl.

In one embodiment for Process B, Step A is conducted at a temperature in a range of from about 20° C. to about 45° C.;

the dehydrating agent used in step A is selected from $PCl_5$, $POCl_3$, $P_2O_5$ and oxalyl chloride;

the base used in step A is selected from a trialkylamine, a pyridine and an imidazole;

Step B is conducted at a temperature in a range of from about 20° C. to about 45° C.;

the base used in step B is selected from an alkali metal carbonate, an alkali metal hydrogen carbonate, an alkali metal bicarbonate, an alkali metal phosphates an alkali metal hydrogen phosphate, an alkali metal hydroxide, a trialkylamine and an aromatic amine.

In another embodiment for Process B, the base used in step A is selected from quinoline, 1-methyl imidazole, 2-picoline, pyridine, 2,6-di-tert-butylpyridine, 2,6-di-tert-butyl-4-methyl pyridine, 2,4-dimethylpyridine, 2,4,6-trimethyl pyridine, triethylamine and diisopropylethylamine; and the base used in step B is selected from $K_2CO_3$, $KHCO_3$, $Na_2CO_3$, $NaHCO_3$, $Na_3PO_4$, $Na_2HPO_4$, $NaH_2PO_4$, $K_3PO_4$, $K_2HPO_4$ and $KH_2PO_4$.

In one embodiment for Process C, the acid used is selected from any acid that can form a crystalline salt with a basic guanidine group, and organic solvent C is selected from toluene, ethyl acetate, isopropyl acetate and acetonitrile.

In another embodiment for Process C, the acid used is selected from 1,5-naphthalene disulfonic acid, p-toluene sulfonic acid and salicylic acid, oxalic acid and tartaric acid.

In another embodiment for Process C, the acid is salicylic acid.

In one embodiment, the present invention provides a process for making a compound of Formula (II) ("Process D"):

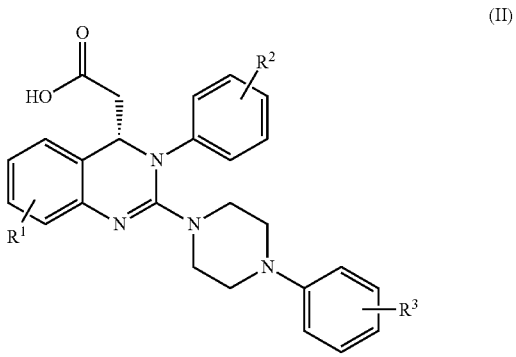

wherein said process comprises the steps:

(A) contacting a compound of formula (I):

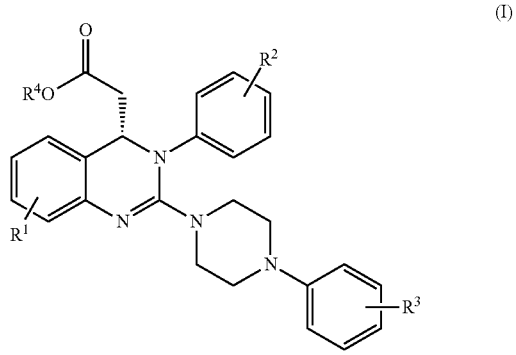

with Di-p-toluoyl-D-tartaric acid in a mixture of organic solvent D and ethyl acetate for a time sufficient to form a compound of formula (ix):

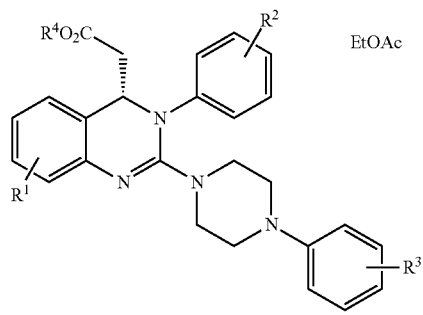

(ix)

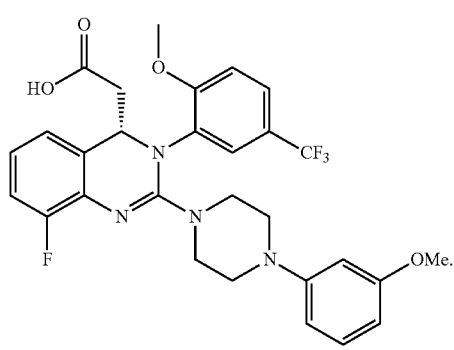

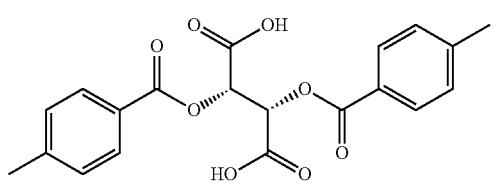

wherein organic solvent D is selected from ethyl acetate, isopropyl acetate, THF, 2-methyltetrahydrofuran, DCM, benzene, toluene, xylene, chlorobenzene, dioxane, and mixtures thereof; and (B) (i) contacting the compound of Formula (ix) with a phosphate or hydrogen phosphate base in water; (ii) contacting the product of step (i) with an alkali metal hydroxide base in a mixture of water, an organic solvent D' and an organic solvent D"; (iii) acidifying the solution of step (ii) using an acid; and (iv) concentrating the solution of step (iii), taking up the concentrate in acetone, and adding the resulting solution to water and collecting the precipitate formed to provide a compound of Formula (II), wherein organic solvent D' is an organic alcohol, and organic solvent D" is an organic ether or THF, and wherein:

$R^1$ represents up to 3 phenyl group substituents, each independently selected from $C_1$-$C_6$ alkyl, $C_1$-$C_6$haloalkyl, halo, —CN, —OH and $C_1$-$C_6$ alkoxy;

$R^2$ represents up to 3 phenyl group substituents, each independently selected from $C_1$-$C_6$ alkyl, $C_1$-$C_6$haloalkyl, halo, —CN, —OH and $C_1$-$C_6$ alkoxy;

$R^3$ represents up to 3 phenyl group substituents, each independently selected from $C_1$-$C_6$ alkyl, $C_1$-$C_6$haloalkyl, halo, —CN, —OH and $C_1$-$C_6$ alkoxy; and $R^4$ is selected from $C_1$-$C_6$ alkyl, and $C_3$-$C_7$ cycloalkyl.

In one embodiment for any of processes A, B, C and D, each occurrence of $R^1$ is halo; each occurrence of $R^2$ is independently selected from halo, $C_1$-$C_3$ alkyl, $C_1$-$C_3$ alkoxy and $C_1$-$C_3$ haloalkyl; each occurrence of $R^3$ is independently selected from $C_1$-$C_3$ alkyl and $C_1$-$C_3$ alkoxy; and $R^4$ is $C_1$-$C_6$ alkyl.

In one embodiment, for Process D, the compound of formula (II) that is made by said process is:

The present invention also provides synthetic intermediates useful for making the Compounds of Formula (I).

In one embodiment, the present invention provides a compound having the structure:

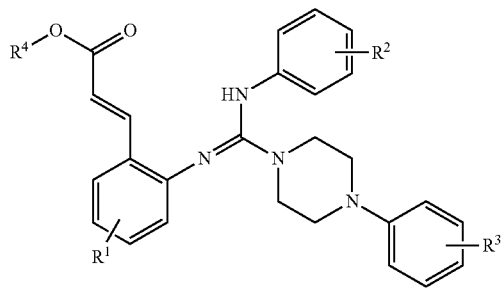

(viii)

or a salt thereof, wherein:

$R^1$ represents up to 3 phenyl group substituents, each independently selected from $C_1$-$C_6$ alkyl, $C_1$-$C_6$haloalkyl, halo, —CN, —OH and $C_1$-$C_6$ alkoxy;

$R^2$ represents up to 3 phenyl group substituents, each independently selected from $C_1$-$C_6$ alkyl, $C_1$-$C_6$haloalkyl, halo, —CN, —OH and $C_1$-$C_6$ alkoxy;

$R^3$ represents up to 3 phenyl group substituents, each independently selected from $C_1$-$C_6$ alkyl, $C_1$-$C_6$haloalkyl, halo, —CN, —OH and $C_1$-$C_6$ alkoxy; and $R^4$ is $C_1$-$C_6$ alkyl or $C_3$-$C_7$ cycloalkyl.

In another embodiment, the present invention provides an acid salt of a compounds of formula (viii).

In another embodiment, the present invention provides the salicylate salt of a compounds of formula (viii).

In still another embodiment, the present invention provides the 1,5-naphthalenedisulfonic acid salt of a compound of formula (viii).

In one embodiment, the present invention provides a compound having the structure:

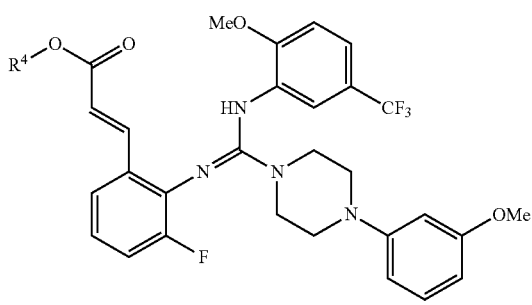

or a salt thereof, wherein $R^4$ is $C_1$-$C_6$ alkyl.

In another embodiment, the present invention provides a compound having the structure:

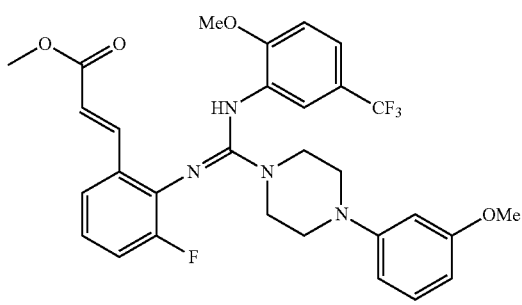 [SMILES: COC(=O)/C=C/c1cccc(F)c1N=C(Nc1cc(C(F)(F)F)ccc1OC)N1CCN(c2cccc(OC)c2)CC1]

or a salt thereof.

In another embodiment, the present invention provides the salicylate salt of the compound having the structure:

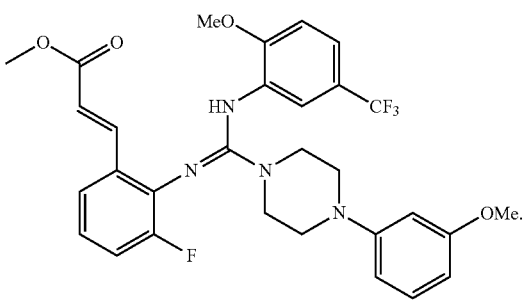 [SMILES: COC(=O)/C=C/c1cccc(F)c1N=C(Nc1cc(C(F)(F)F)ccc1OC)N1CCN(c2cccc(OC)c2)CC1]

In still another embodiment, the present invention provides the salicylate salt of the compound having the structure:

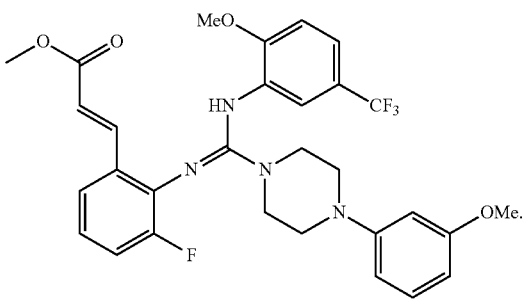 [SMILES: COC(=O)/C=C/c1cccc(F)c1N=C(Nc1cc(C(F)(F)F)ccc1OC)N1CCN(c2cccc(OC)c2)CC1]

In yet another embodiment, the present invention provides the 1,5-naphthalenedisulfonic acid salt of the compound having the structure:

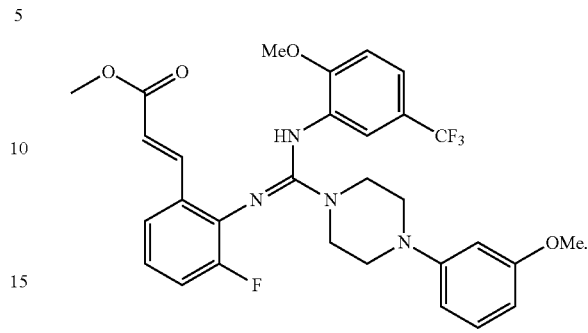

Unlike the synthetic pathways described in U.S. Pat. Nos. 7,196,086 and 8,084,604, the processes of the present invention employs fewer steps and provides an improved yield of Compound A with a high degree of stereoselectivity.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% $CH_3CN$, 5 minutes—95% $CH_3CN$, 5-7 minutes—95% $CH_3CN$, 7 minutes—stop. The retention time and observed parent ion are given.

Example 1

Preparation of Intermediate Compound 2

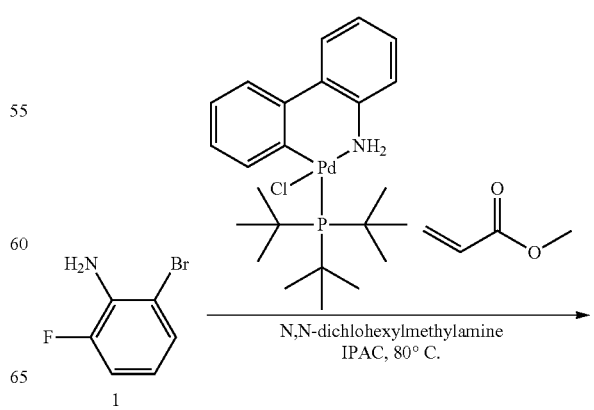

-continued

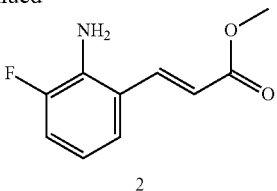

To a degassed solution of 2-bromo-6-fluoroaniline (1, 99.5 g, 0.524 mol), methyl acrylate (95.0 mL, 1.05 mol), Chloro[(tri-tert-butylphosphine)-2-(2-aminobiphenyl)] palladium(II) (0.537 g, 1.05 mmol) in isopropyl acetate (796 mL), was added degassed N,N-dicyclohexylmethylamine (135 mL, 0.628 mol). The resulting reaction was heated to 80° C. and allowed to stir at this temperature for 5 hours. The resulting slurry was cooled to 20° C. and filtered. The filtrate was washed with 1 M citric acid to provide a solution that contained compound 2 (99.3 g, 97% assay yield) in isopropyl acrylate, which was used without further purification. $^1$H NMR (500 MHz, d-CHCl$_3$): $\delta_H$ 7.79 ppm (1H, d, J=15.9 Hz), 7.17 ppm (1H, d, J=8.2 Hz), 7.00 ppm (1H, ddd, J=10.7, 8.2, 1.2 Hz), 6.69 ppm (1H, td, J=8.2, 5.1 Hz), 6.38 ppm (1H, d, J=15.9 Hz), 4.06 ppm (2H, br s), 3.81 ppm (3H, s).

Example 2

Preparation of Intermediate Compound 3

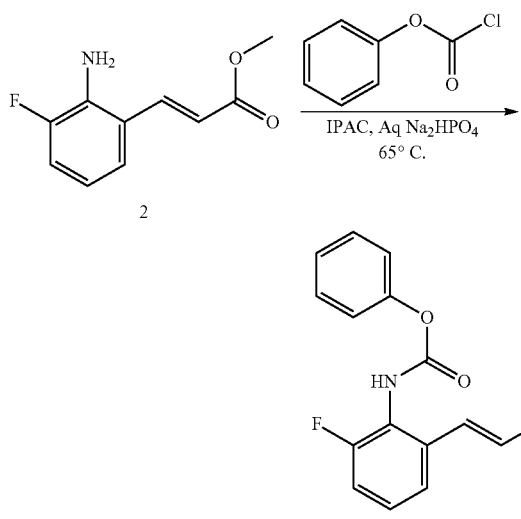

To a solution of compound 2 (48.8 g, 0.250 mol) in 683 mL of isopropyl acetate was added 244 mL of water, followed by di-sodium hydrogen phosphate (53.2 g, 0.375 mol). To the resulting solution was added phenyl chloroformate (39.2 mL, 0.313 mol) dropwise over 30 minutes. The resulting reaction was heated to 30° C. and allowed to stir at this temperature for 5 hours for 4 hours and then was heated to 60° C. and allowed to stir at this temperature for 5 hours for an additional 2 hours to remove excess phenyl chloroformate. An additional 293 mL of isopropyl acetate was then added and the reaction mixture was allowed to stir at room temperature until the solids completely dissolved into solution. The resulting reaction mixture was transferred to a separatory funnel and the organic phase was washed with 98 mL of water and collected to provide a solution of compound 3 in isopropyl acetate, which was used without further purification. $^1$H NMR (500 MHz, d-acetonitrile): $\delta_H$ 7.91 ppm (1H, d, J=15.9 Hz), 7.85 ppm (1H, br s), 7.63 ppm (1H, d, J=7.9 Hz), 7.45-7.39 ppm (3H, m), 7.33-7.27 ppm (2H, m), 7.21 ppm (2H, br), 6.60 ppm (1H, d, J=16.0 Hz).

Example 3

Preparation of Intermediate Compound 4

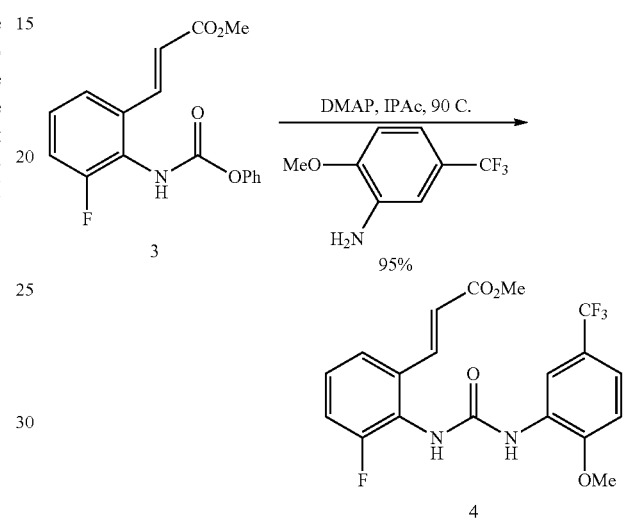

A solution of compound 3 (79.0 g, 0.250 mol), 2-methoxy-5-(trifluoromethyl)aniline (52.7 g, 0.276 mol), and 4-dimethylaminopyridine (0.92 g, 0.0075 mol) in isopropyl acetate (780 mL) was heated to reflux and allowed to stir at this temperature for 5 hours. The resulting slurry was cooled to 20° C., then allowed to stir at this temperature for for two hours at this temperature, then filtered. The collected filter cake was dried in vacuo to provide compound 5 (95.0 g, 0.230 mol) as a white solid, which was used without further purification. $^1$H NMR (500 MHz, d-TFA): $\delta_H$ 7.98 ppm (1H, d, J=16.1 Hz), 7.87 ppm (1H, s), 7.47 ppm (1H, d, J=7.9 Hz), 7.41 ppm (1H, d, J=8.5 Hz), 7.35 ppm (1H, q, J=8.5 Hz), 7.19 ppm (1H, t, J=8.6 Hz), 6.98 ppm (1H, d, J=8.6 Hz), 6.56 ppm (1H, d, J=16.0 Hz), 3.85 ppm (6H, br s).

Example 4

Preparation of Intermediate Compound 6

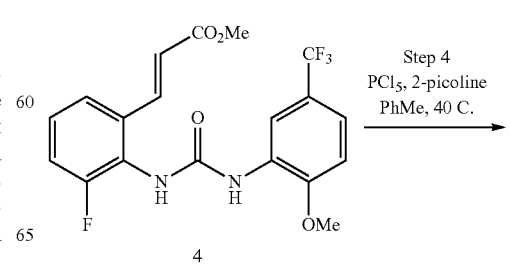

-continued

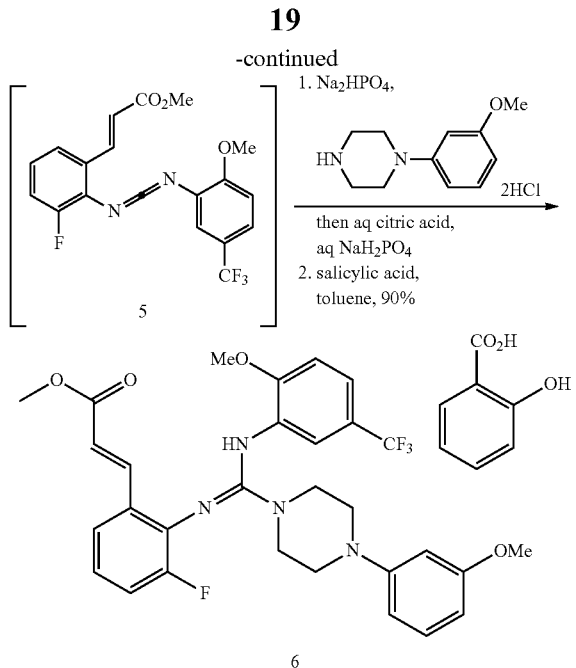

To a stirred suspension of compound 4 (14.0 g, 34.0 mmol) in toluene (140 mL) at room temperature was added 2-picoline (10.1 mL, 102 mmol) followed by PCl$_5$ (8.19 g, 37.3 mmol). The resulting reaction was heated to 40° C. and allowed to stir at this temperature for 4 hours, then was cooled to 0° C. and cautiously (internal temperature kept <15° C.) quenched with KOH (2 M, 102 mL). The resulting solution was allowed to warm to room temperature, allowed to stir for 30 minutes, then was filtered and the filtrate transferred to a separatory funnel. The organic phase was washed sequentially with H$_3$PO$_4$ (1M, 50 mL) and H$_2$O (50 mL) to provide a solution of compound 5 in toluene, which was used without further purification. $^1$H NMR (500 MHz, d$_6$-DMSO): $\delta_H$ 7.96 (1H, d, J=16.2 Hz), 7.74 (1H, d, J=7.9 Hz), 7.61 (1H, dd, J=6.7, 1.6 Hz), 7.50 (1H, d, J=1.9 Hz), 7.43 (1H, t, J=9.2 Hz), 7.30 (1H, d, J=8.4 Hz), 7.28 (1H, m), 6.79 (1H, d, J=16.2 Hz), 3.91 (3H, s), 3.74 (3H, s).

To the solution of compound 5 at room temperature was added an aqueous solution of piperazine hydrochloride (0.40 M, 93.3 mL, 37.3 mmol) followed by Na$_2$HPO$_4$ (14.5 g, 102 mmol). The resulting reaction was allowed to stir for 1 hour at room temperature, then transferred to a separatory funnel. The organic phase was washed sequentially with NaH$_2$PO$_4$ (50 mL) and H$_2$O (50 mL). Salicylic acid (5.16 g, 37.3 mmol) was then added to the organic phase, and the resulting solution was cooled to 0° C. and allowed to stir at this temperature for 1 hour to provide a slurry which was filtered and washed with cold toluene (50 mL). The filter cake was dried under air to provide compound 6 (23.0 g, 31.7 mmol, 93%) as a white crystalline solid: $^1$H NMR (500 MHz, d$_6$-DMSO): $\delta_H$ 12.9 (1H, br s), 7.75 (1H, dd, J=7.8, 1.8 Hz), 7.72 (1H, d, J=16.1 Hz), 7.40 (1H, td, J=7.2, 1.7 Hz), 7.27 (1H, d, J=7.8 Hz), 7.17 (1H, m), 7.16 (1H, t, J=8.2 Hz), 7.02 (1H, br s), 6.95 (1H, t, J=8.6 Hz), 6.88-6.81 (3H, m), 6.78 (1H, br s), 6.60 (1H, dd, J=8.2, 2.0 Hz), 6.54 (1H, m), 6.48 (1H, d, J=16.1 Hz), 6.43 (1H, dd, J=8.0, 2.1 Hz), 3.73 (3H, s), 3.71 (3H, s), 3.69 (4H, br s), 3.68 (3H, s).

Free Base: $^1$H NMR (500 MHz, CD$_3$CN): $\delta_H$ 7.91 (1H, d, J=16.1 Hz), 7.29 (1H, d, J=8.0 Hz), 7.24 (1H, d, J=1.4 Hz), 7.20 (1H, t, J=8.1 Hz), 7.15 (1H, dd, J=8.6, 1.4 Hz), 6.94 (1H, m), 6.92 (1H, t, J=8.1 Hz), 6.80 (1H, td, J=8.1, 5.4 Hz), 6.60 (1H, dd, J=8.3, 2.2 Hz), 6.54 (1H, t, J=2.2 Hz), 6.50 (1H, d, J=16.1 Hz), 6.47 (2H, m), 3.80 (3H, s), 3.79 (3H, s), 3.72 (3H, s), 3.63 (4H, t, J=5.1 Hz), 3.25 (4H, t, J=5.0 Hz).

2:1 NDSA Salt: $^1$H NMR (500 MHz, d$_6$-DMSO): $\delta_H$ 10.2 (2H, br s), 8.86 (1H, d, J=8.6 Hz), 7.92 (1H, d, J=7.0 Hz), 7.47-7.37 (4H, m), 7.27-7.14 (4H, m), 6.96 (1H, d, J=8.6 Hz), 6.65 (1H, d, J=8.3 Hz), 6.59 (1H, s), 6.54 (1H, d, J=15.9 Hz), 6.47 (1H, d, J=8.3 Hz), 3.91 (4H, m), 3.77 (3H, s), 3.76 (3H, s), 3.74 (3H, s), 3.43 (4H, m). 1,5-naphthalene disulfonic acid Example 5

Preparation of Intermediate Compound 7

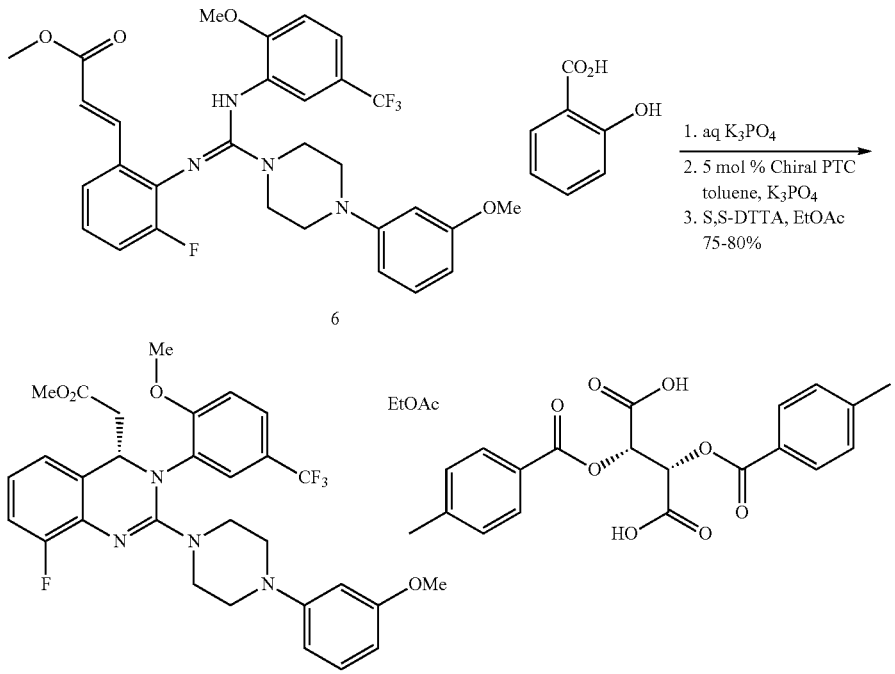

To a suspension of compound 6 (12.5 g, 16.6 mmol) in 125 mL of toluene was added 50 mL of 0.43M aqueous $K_3PO_4$. The resulting reaction was allowed to stir for 1 hour at room temperature and the reaction mixture was transferred to a separatory funnel. The organic phase was collected, washed once with 30 mL 0.43M aqueous $K_3PO_4$ then cooled to 0° C. and aqueous $K_3PO_4$ (60 mL, 0.43 M, 25.7 mmol) was added. To the resulting solution was added a room temperature solution of ((1S,2S,4S,5R)-1-(3,5-bis(trifluoromethyl)benzyl)-2-((R)-hydroxyl(1-(3-(trifluoromethyl)benzyl)quinolin-1-ium-4-yl)methyl)-5-vinylquinuclidin-1-ium bromide) (0.704 g, 0.838 mmol) in 1.45 mL of DMF. The resulting reaction was allowed to stir at 0° C. until the reaction was complete (monitored by HPLC), then the reaction mixture was transferred to a separatory funnel and the organic phase was collected and washed sequentially with 1M glycolic acid (25 mL) and water (25 mL). The organic phase was filtered through solka flok and concentrated in vacuo to a total volume of 60 mL. Ethyl acetate (20 mL) was added to the resulting solution, followed by (S,S)-Di-P-Toluoyl-D-tartaric acid (5.61 g, 14.1 mmol). Penultimate seed (0.2 g) was added the resulting solution was allowed to stir at room temperature for 12 hours. The solution was then filtered and the collected solid was washed twice with ethyl acetate, then dried in vacuo to provide compound 7 as its DTTA salt ethyl acetate solvate (13.8 g, 78%). $^1$H NMR (500 MHz, $d_6$-DMSO): $\delta_H$ 13.95 (2H, br s), 7.90 (4H, d, J=8.1 Hz), 7.55 (1H, dd, J=8.6, 1.3 Hz), 7.38 (4H, d, J=8.1 Hz), 7.26 (1H, d, J=7.8 Hz), 7.09-7.05 (3H, m), 6.91-6.86 (2H, m), 6.44 (1H, dd, J=8.2, 1.7 Hz), 6.39 (1H, t, J=2.0 Hz), 6.36 (1H, dd, J=8.2, 2.0 Hz), 5.82 (2H, s), 4.94 (1H, t, J=7.1 Hz), 4.02 (2H, q, J=7.1 Hz), 3.83 (3H, br s), 3.68 (3H, s), 3.64 (3H, s), 3.47 (2H, br s), 3.37 (2H, br s), 2.95 (2H, br s), 2.87-2.80 (3H, m), 2.56 (1H, dd, J=14.3, 7.0 Hz), 2.39 (6H, s), 1.98 (3H, s), 1.17 (3H, t, J=7.1 Hz).

Example 6

Preparation of Compound A

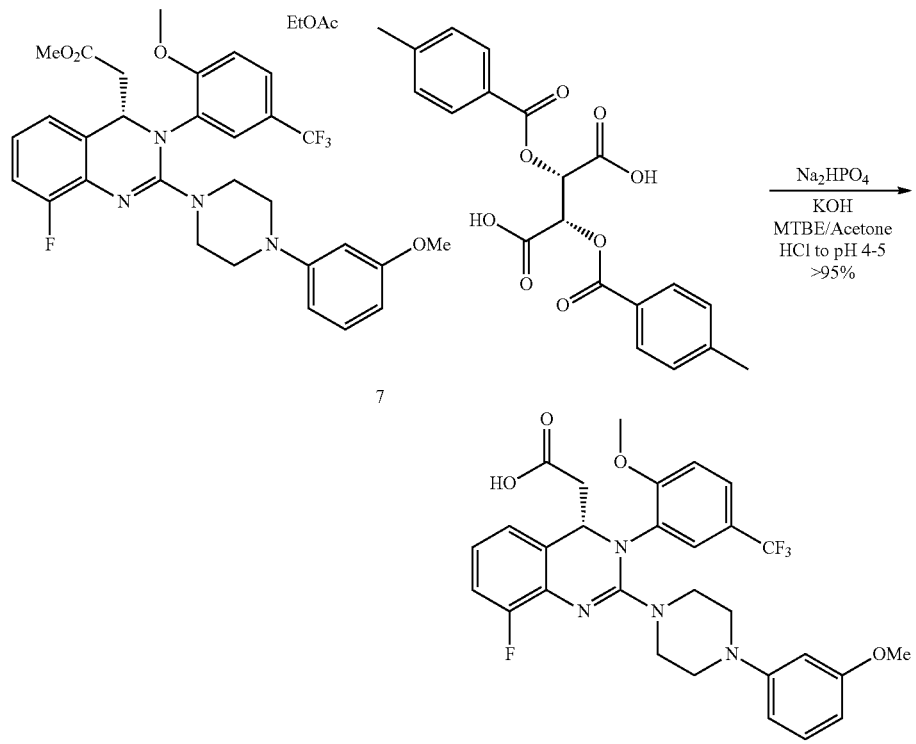

To a slurry of compound 7 (20 g, 18.9 mmol) in MTBE (40.0 mL) at room temperature was added a solution of sodium phosphate dibasic dihydrate (8.42 g, 47.3 mmol) in water (80 mL) and the resulting slurry was allowed to stir at room temperature for 40 minutes. The reaction mixture was transferred to a separatory funnel and the organic phase was collected and washed with a solution of sodium phosphate dibasic dihydrate (3.37 g, 18.91 mmol) in water (40.0 mL). A solution of KOH (4.99 g, 76 mmol) in water (80 mL) and methanol (10.00 mL) was then added to the organic phase and the resulting mixture was heated to 50° C. and allowed to stir at this temperature for 6 hours. MTBE (20 mL) and water (40 mL) were then added to the reaction mixture and the resulting solution was transferred to a separatory funnel and the aqueous layer was collected and washed with MTBE (20 mL). Additional MTBE (40 mL) was added to the aqueous layer and the resulting solution was adjusted to pH 4-5 via slow addition of concentrated HCl. The resulting acidified solution was transferred to a separatory funnel and the organic phase was collected, concentrated in vacuo and solvent switched with acetone, maintaining a 30 mL volume. The resulting acetone solution was added dropwise to water and the precipitate formed was filtered to provide compound A as a white solid (10 g, 92%). $^1$H NMR (500 MHz, $d_6$-DMSO): $\delta_H$ 12.6 (1H, s), 7.52 (1H, dd, J=8.6, 1.3 Hz), 7.41 (1H, brs), 7.22 (1H, d, J=7.2 Hz), 7.08-7.02 (2H, m), 6.87-6.84 (2H, m), 6.44 (1H, dd, J=8.3, 1.8 Hz), 6.39 (1H, t, J=2.1 Hz), 6.35 (1H, dd, J=8.1, 2.0 Hz), 4.89 (1H, t, J=7.3 Hz), 3.79 (3H, br s), 3.68 (3H, s), 3.47 (2H, br s), 3.39 (2H, br s), 2.96-2.93 (2H, m), 2.82-2.77 (3H, m), 2.44 (1H, dd, J=14.8, 7.4 Hz).

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A process for making a compound of Formula (I):

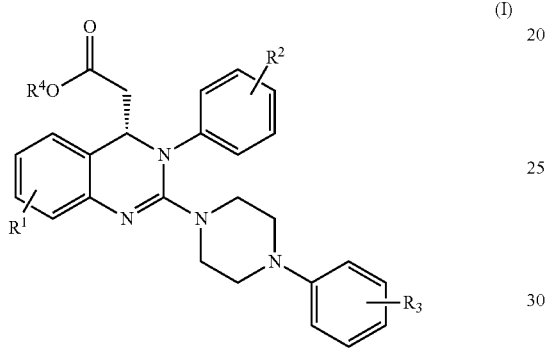

(I)

wherein said process comprises contacting a compound of formula (viii):

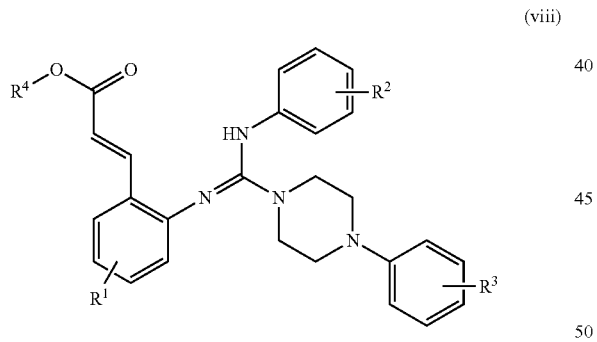

(viii)

or a salt thereof,
with a phase-transfer catalyst and a base, in a mixture of water and organic solvent A, for a time sufficient to form a compound of formula (I), wherein:
  $R^1$ represents 0 to 3 phenyl group substituents, each independently selected from $C_1$-$C_6$ alkyl, $C_1$-$C_6$haloalkyl, halo, —CN, —OH and $C_1$-$C_6$ alkoxy;
  $R^2$ represents 0 to 3 phenyl group substituents, each independently selected from $C_1$-$C_6$ alkyl, $C_1$-$C_6$haloalkyl, halo, —CN, —OH and $C_1$-$C_6$ alkoxy;
  $R^3$ represents 0 to 3 phenyl group substituents, each independently selected from $C_1$-$C_6$ alkyl, $C_1$-$C_6$haloalkyl, halo, —CN, —OH and $C_1$-$C_6$ alkoxy; and
  $R^4$ is $C_1$-$C_6$ alkyl or $C_3$-$C_7$ cycloalkyl,
wherein:
  organic solvent A is selected from toluene, DCM, MTBE, 2-methyltetrahydrofuran, xylenes, ethyl acetate, isopropyl acetate, acetonitrile and mixtures thereof;
  the base is selected from an alkali metal carbonate, an alkali metal hydrogen carbonate, an alkali metal bicarbonate, an alkali metal phosphate, an alkali metal hydrogen phosphate, an alkali metal hydroxide, a trialkylamine and an aromatic amine;
organic solvent A is selected from toluene, DCM, MTBE, 2-methyltetrahydrofuran, xylenes and mixtures thereof; and
  the phase-transfer catalyst is a compound of formula (PT1) or (PT2):

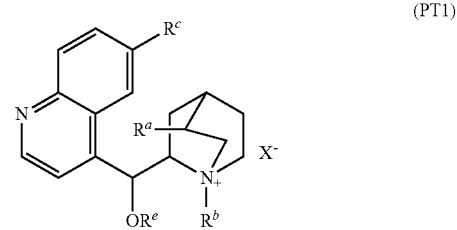

(PT1)

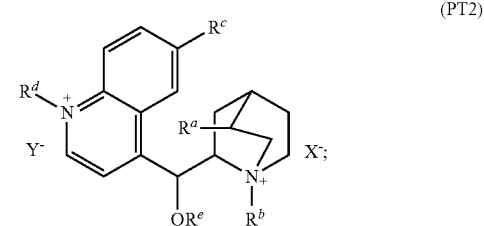

(PT2)

wherein:
  $R^a$ is selected from ethyl and vinyl,
  $R^b$ is selected from $C_{1-6}$alkyl, $C_{2-6}$alkenyl, $C_{2-6}$alkynyl, $C_{3-6}$cycloalkyl, aryl, 5 or 6-membered monocyclic heteroaryl, 9 or 10-membered bicyclic heteroaryl, —$C_{1-4}$alkyl-aryl, —$C_{1-4}$alkyl-(5 or 6-membered monocyclic heteroaryl) and $C_{1-4}$alkyl-(9 or 10-membered bicyclic heteroaryl), wherein $C_{1-6}$alkyl, $C_{2-6}$alkenyl, $C_{2-6}$alkynyl, $C_{3-6}$cycloalkyl, aryl, heteroaryl and the aryl and heteroaryl portions of —$C_{1-4}$alkyl-aryl, —$C_{1-4}$alkyl-(5 or 6-membered monocyclic heteroaryl), and $C_{1-4}$alkyl-(9 or 10-membered bicyclic heteroaryl), are optionally substituted with one to five substituents independently selected from $R^f$,
  $R^c$ is selected from hydrogen, methoxy, halo, —CN, —$NO_2$ and —$CF_3$;
  $R^d$ is selected from the group consisting of hydrogen, C(O)R, C(O)OR, CONRR', and $C_{1-6}$alkyl,
  $R^e$ is selected from $C_{1-6}$alkyl, $C_{2-6}$alkenyl, $C_{2-6}$alkynyl, $C_{3-6}$cycloalkyl, aryl, 5 or 6-membered monocyclic heteroaryl, 9 or 10-membered bicyclic heteroaryl, —C$_{1-4}$alkyl-aryl, —C$_{1-4}$alkyl-(5 or 6-membered monocyclic heteroaryl) and C$_{1-4}$alkyl-(9 or 10-membered bicyclic heteroaryl), wherein C$_{1-6}$alkyl, C$_{2-6}$alkenyl, C$_{2-6}$alkynyl, C$_{3-6}$cycloalkyl, aryl, heteroaryl and the aryl and heteroaryl portions of —C$_{1-4}$alkyl-aryl, —C$_{1-4}$alkyl-(5 or 6-membered monocyclic heteroaryl), and C$_{1-4}$alkyl-(9 or 10-membered bicyclic heteroaryl), are optionally substituted with one to five substituents independently selected from R$^f$, each occurrence of R$^f$ is independently selected from the group consisting of C$_{1-4}$ alkyl, C$_{1-4}$ haloalkyl, aryl, C$_{1-4}$ alkoxy, hydroxy, CN, CO$_2$R, CONRR', SR, SO$_2$R, SO$_3$R, PR$_2$, PO(OR)$_2$, PO(OR) (NRR'), PO(NRR')$_2$, P(OR)$_2$, P(OR)(NRR'), P(NRR')$_2$, SiRR'R'', B(OR)$_2$, C(O)R, NRR', NO$_2$, and halogen, each R, R' and R'' is independently selected from the group consisting of, H, C$_{1-6}$alkyl, hydroxyl, C$_{1-6}$alkoxy, aryl, 5 or 6-membered monocyclic heteroaryl, 9 or 10-membered bicyclic heteroaryl, —CH$_2$-aryl, —CH$_2$-heteroaryl, and each X and Y are independently anions selected from halide, OH, HSO$_4$, SO$_4$, BF$_4$, SbF$_6$, carboxylate, carbonate, hydrogen carbonate, NO$_3$, sulfonate, hexafluorophosphate, phosphate, hydrogen phosphate and perchlorate.

2. The process of claim 1, further comprising the step of making the compound of formula (viii)

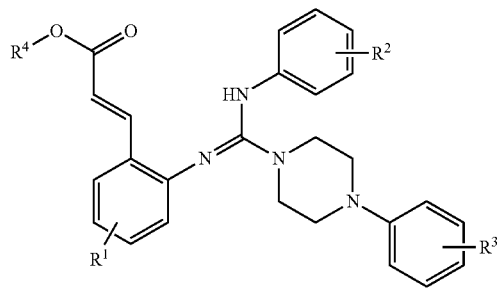

(viii)

wherein said process comprises the steps:

(A) contacting a compound of Formula (v):

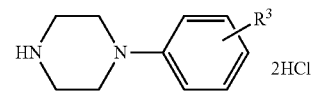

(v)

with a dehydrating agent and a base in an organic solvent B, for a time sufficient to provide an intermediate compound of Formula (vi):

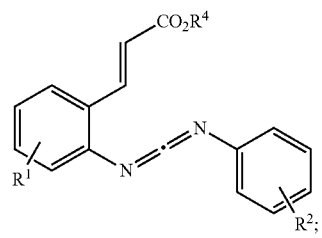

(vi)

and (B) contacting the intermediate compound of formula (vi) with a compound of formula (vii):

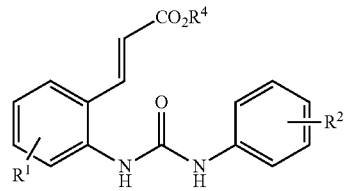

(vii)

in the presence of a base, in a mixture of water and organic solvent B', for a time sufficient to provide a compound of formula (viii), wherein organic solvents B and B' are each independently selected from ethyl acetate, isopropyl acetate, THF, 2-methyltetrahydrofuran, DCM, benzene, toluene, xylene, chlorobenzene, acetonitrile and dioxane.

3. The process of claim 2, further comprising the step of contacting the formed compound of formula (viii) with an acid, in a mixture of water and an organic solvent C for a time sufficient to form the corresponding acid salt of the compound of formula (viii), wherein organic solvent C is selected from toluene, DCM, MTBE, 2-methyltetrahydrofuran, xylenes, ethyl acetate, isopropyl acetate, acetonitrile and mixtures thereof, to provide the corresponding acid salt of the compound of formula (viii).

4. The process of claim 1, wherein said process is conducted at a temperature in a range of from about −10° C. to about 30° C.

5. The process of claim 4, wherein:

said process is conducted at a temperature in a range of from about −5° C. to about 10° C.;

the base used is selected from K$_2$CO$_3$, KHCO$_3$, Na$_2$CO$_3$, NaHCO$_3$, Na$_3$PO$_4$, Na$_2$HPO$_4$, NaH$_2$PO$_4$, K$_3$PO$_4$, K$_2$HPO$_4$ and KH$_2$PO$_4$; and the phase transfer catalyst used is selected from:

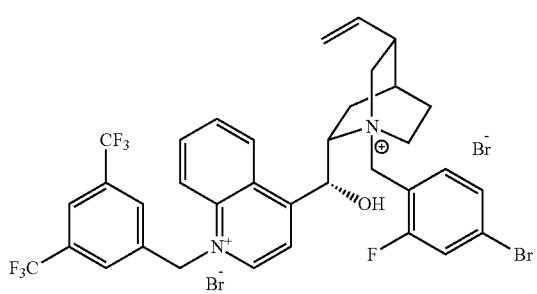

-continued

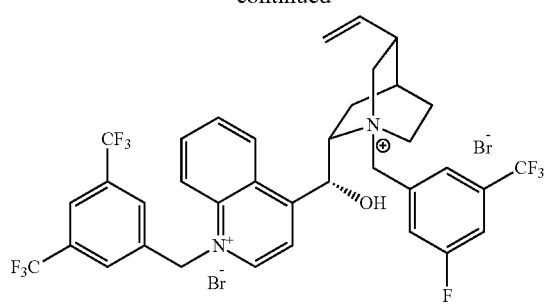

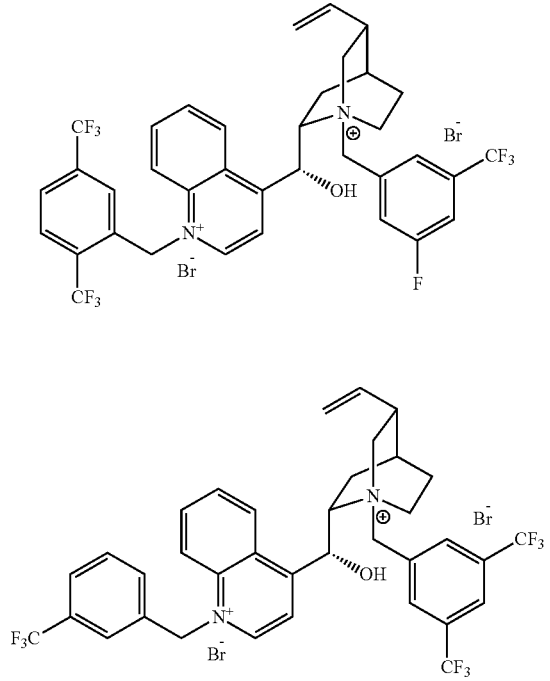

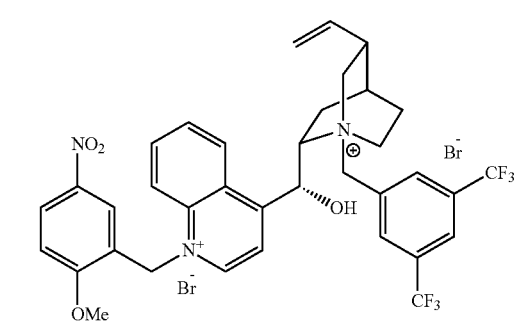

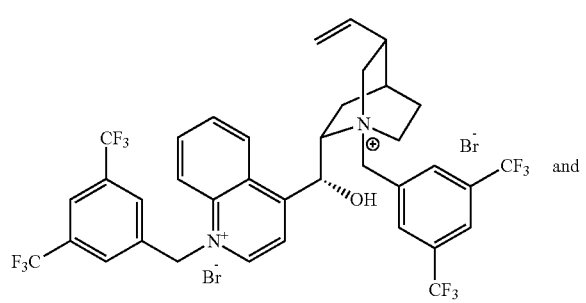
and

-continued

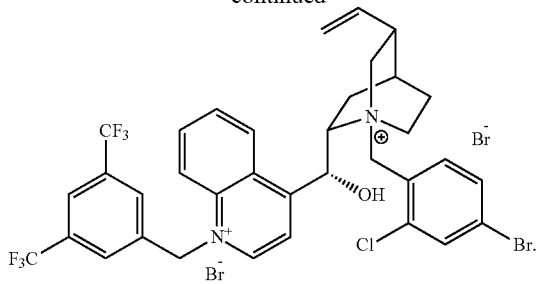

6. The process of claim 1, wherein the phase transfer catalyst used is:

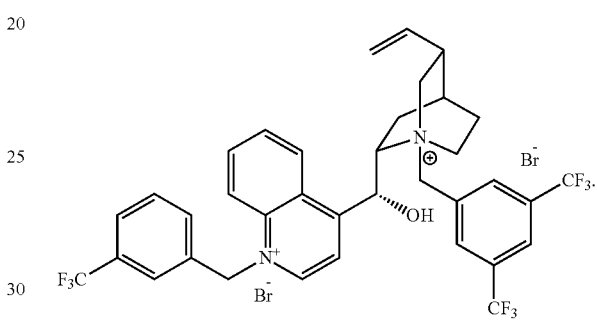

7. The process of claim 2, wherein:
Step A is conducted at a temperature in a range of from about 20° C. to about 45° C.;
the dehydrating agent used in step A is selected from $PCl_5$, $POCl_3$, $P_2O_5$ and oxalyl chloride;
the base used in step A is selected from a trialkylamine, a pyridine and an imidazole;
Step B is conducted at a temperature in a range of from about 20° C. to about 45° C.; and
the base used in step B is selected from an alkali metal carbonate, an alkali metal hydrogen carbonate, an alkali metal bicarbonate, an alkali metal phosphates an alkali metal hydrogen phosphate, an alkali metal hydroxide, a trialkylamine and an aromatic amine.

8. The process of claim 7, wherein:
the base used in step A is selected from quinoline, 1-methyl imidazole, 2-picoline, pyridine, 2,6-di-tert-butylpyridine, 2,6-di-tert-butyl-4-methyl pyridine, 2,4-dimethylpyridine, 2,4,6-trimethyl pyridine, triethylamine and diisopropylethylamine; and
the base used in step B is selected from $K_2CO_3$, $KHCO_3$, $Na_2CO_3$, $NaHCO_3$, $Na_3PO_4$, $Na_2HPO_4$, $NaH_2PO_4$, $K_3PO_4$, $K_2HPO_4$ and $KH_2PO_4$.

9. The process of claim 3, wherein the acid used is selected from any acid that can form a crystalline salt with a basic guanidine group, and organic solvent C is selected from toluene, ethyl acetate, isopropyl acetate and acetonitrile.

10. The process of claim 3, wherein the acid used is selected from 1,5-naphthalene disulfonic acid, p-toluene sulfonic acid and salicylic acid, oxalic acid and tartaric acid.

11. The process of claim 10, wherein the acid is salicylic acid.

12. The process of claim 1, wherein each occurrence of $R^1$ is halo; each occurrence of $R^2$ is independently selected from halo, $C_1$-$C_3$ alkyl, $C_1$-$C_3$ alkoxy and $C_1$-$C_3$ haloalkyl; each occurrence of $R^3$ is independently selected from $C_1$-$C_3$ alkyl and $C_1$-$C_3$ alkoxy; and $R^4$ is $C_1$-$C_6$ alkyl.

13. The process of claim 1, wherein the compound of formula (I) made by said process is:

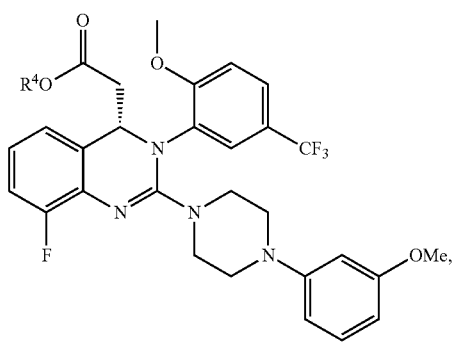

wherein $R^4$ is $C_1$-$C_6$ alkyl.

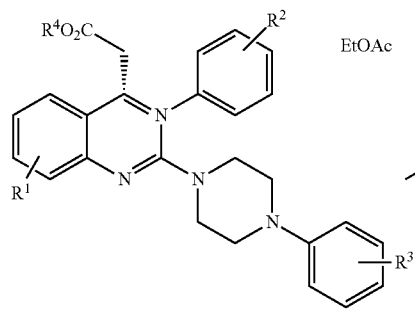

14. The process of claim 13, wherein for the compound of formula (I) made by said process, $R^4$ is methyl.

15. A process for making a compound of Formula II:

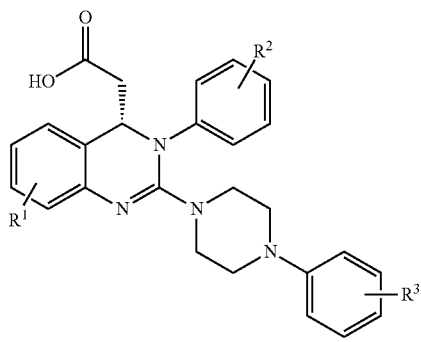

wherein said process comprises the steps:

(A) contacting a compound of formula (I):

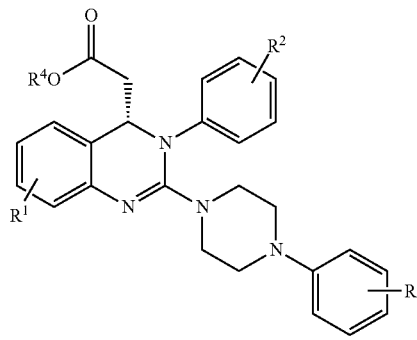

with Di-p-toluoyl-D-tartaric acid in a mixture of organic solvent D and ethyl acetate for a time sufficient to form a compound of formula (ix):

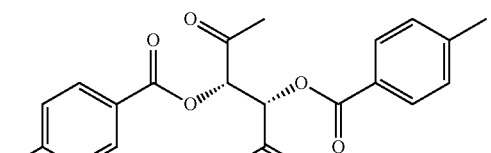

wherein organic solvent D is selected from ethyl acetate, isopropyl acetate, THF, 2-methyltetrahydrofuran, DCM, benzene, toluene, xylene, chlorobenzene, dioxane, and mixtures thereof; and (B) (i) contacting the compound of Formula (ix) with a phosphate or hydrogen phosphate base in water; (ii) contacting the product of step (i) with an alkali metal hydroxide base in a mixture of water, an organic solvent D' and an organic solvent D"; (iii) acidifying the solution of step (ii) using an acid; and (iv) concentrating the solution of step (iii), taking up the concentrate in acetone, and adding the resulting solution to water and collecting the precipitate formed to provide a compound of Formula (II), wherein organic solvent D' is an organic alcohol, and organic solvent D" is an organic ether or THF, and wherein:

$R^1$ represents 0 to 3 phenyl group substituents, each independently selected from $C_1$-$C_6$ alkyl, $C_1$-$C_6$ haloalkyl, halo, —CN, —OH and $C_1$-$C_6$ alkoxy;

$R^2$ represents 0 to 3 phenyl group substituents, each independently selected from $C_1$-$C_6$ alkyl, $C_1$-$C_6$ haloalkyl, halo, —CN, —OH and $C_1$-$C_6$ alkoxy;

R³ represents 0 to 3 phenyl group substituents, each independently selected from C₁-C₆ alkyl, C₁-C₆haloalkyl, halo, —CN, —OH and C₁-C₆ alkoxy; and
R⁴ is selected from C₁-C₆ alkyl, and C₃-C₇ cycloalkyl.
16. The process of claim 15, wherein the compound of formula (II) that is made by said process is:
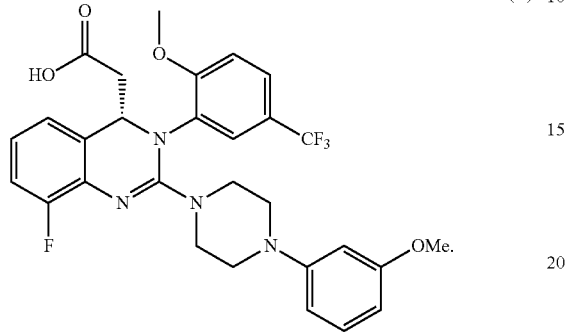
(II)
* * * * *